United States Patent [19]

Mueller-Kirschbaum et al.

[11] Patent Number: 5,503,682

[45] Date of Patent: Apr. 2, 1996

[54] PROCESS FOR DEGREASING AND CLEANING METAL SURFACES

[75] Inventors: Thomas Mueller-Kirschbaum, Solingen; Wolfgang Hater; Dieter Knapp, both of Duesseldorf; Thomas Vienenkoetter, Essen, all of Germany

[73] Assignee: Henkel Kommanditgesellschaft auf Aktien, Duesseldorf, Germany

[21] Appl. No.: 232,274

[22] PCT Filed: Oct. 28, 1992

[86] PCT No.: PCT/EP92/02462

§ 371 Date: May 5, 1994

§ 102(e) Date: May 5, 1994

[87] PCT Pub. No.: WO93/09264

PCT Pub. Date: May 13, 1993

[30] Foreign Application Priority Data

Nov. 6, 1991 [DE] Germany .................. 41 36 442.2

[51] Int. Cl.⁶ .................................................. B08B 3/02
[52] U.S. Cl. .................................. 134/2; 134/10; 134/40
[58] Field of Search .............................. 134/40, 2, 3, 10

[56] References Cited

U.S. PATENT DOCUMENTS

| | | | |
|---|---|---|---|
| 3,150,518 | 9/1964 | Peterson | 73/53 |
| 4,276,094 | 6/1981 | Gutnick et al. | 134/10 |
| 5,188,135 | 2/1993 | Neumann et al. | 134/64 R |
| 5,404,606 | 4/1995 | Mueller-Kirschbaum et al. | 8/158 |

FOREIGN PATENT DOCUMENTS

| | | |
|---|---|---|
| 0149500 | 7/1985 | European Pat. Off. . |
| 0264867 | 7/1988 | European Pat. Off. . |
| 3424711 | 2/1986 | Germany . |

OTHER PUBLICATIONS

Journal of Applied Science vol. 28, 1983, Schork, Ray "On-Line Measurement of Surface Tension and Density with Aplications to Emulsion Polymerization" pp. 407–430.
Kresse et al., "Säuberung technischer Oberflächen, Kontakt & studium", vol. 264, Expert Verlag 1988.

*Primary Examiner*—Melvyn Andrews
*Attorney, Agent, or Firm*—Wayne C. Jaeschke; Norvell E. Wisdom; Real J. Grandmaison

[57] ABSTRACT

The invention relates to a process for degreasing and cleaning metal surfaces with surfactant containing aqueous cleaning liquids in baths and/or by spraying. In order to obtain an exact measurement of the bath load and cleaning reserve economically and quickly to allow more accurate subsequent metering of the cleaning agent, the invention provides that, as a measure of the current reserve of cleaning liquid, a bubble tensiometer is used to measure a value correlated with the dynamic surface tension and operated with a sufficiently constant gas flow, the measurements are compared with a predetermined set value obtained for the cleaning agent used by calibration, and, depending on the results of comparison, appropriate steps are taken to treat the cleaning liquid.

11 Claims, 6 Drawing Sheets

PROCESS FOR DEGREASING AND CLEANING METAL SURFACES

FIELD OF THE INVENTION

This invention relates to a process for degreasing and cleaning metal surfaces using surfactant-containing water-based cleaning liquids in baths and/or by spray cleaning, optionally followed by rinsing of the degreased and cleaned surfaces. In spray cleaning, the cleaning liquid is normally recirculated.

STATEMENT OF RELATED ART

Metal parts, for example plates, have to be freed from surface residues after machining and before any subsequent surface treatment, for example electroplating. Apart from small metal particles, it is mainly fats and oils of natural or mineral origin, which have been used as drilling and cutting aids or as lubricants in preceding treatment steps, that have to be removed.

The surface is freed from the various soil types, above all from the fats and oils, typically in water-based cleaning baths which generally contain surface-active components, for example nonionic surfactants. Both dip cleaning and spray cleaning methods are applied. A review of the cleaning preparations typically used, also known as cleaners, can be found for example in J. Kresse et al., "Säuberung technischer Oberflächen" [Title in English: Cleaning of Technical Surfaces], *Kontakt & Studium* Vol. 264 (Expert Verlag).

The performance of the cleaning baths decreases with increasing degree of soiling. In addition, part of the cleaning liquid is removed by the parts to be cleaned. Beyond a certain bath soiling level, the necessary cleaning performance is no longer guaranteed. Bath servicing measures have to be taken to keep the cleaning performance of the bath at its original level. This is done on the one hand by replenishment of the cleaning preparation as a whole or individual components thereof and, on the other hand, by removal of the various soil types from the cleaning liquids. Typical processes for the removal of oils from the cleaning bath are carried out inter alia with skimmers, separators, oil separators, centrifuges, evaporators or by membrane techniques, for example microfiltration or ultrafiltration.

However, because the various bath soils and also the separators interact with the ingredients of the cleaning preparations, not only the soils, but also some of the cleaning components are also removed from the solution, so that the components in question have to be replenished to guarantee the required cleaning effect.

Monitoring the cleaning baths, i.e. measurement of the bath soiling level and the cleaning reserves still present, is crucially important to bath servicing measures. This is because, on the one hand, it is important to keep to the optimal time for replacing the bath. The optimal replacement time arrives when the soiled cleaning liquid fails to provide a satisfactory cleaning result in the next cleaning operation. On the other hand, only that quantity of cleaning preparation or components thereof which is required to obtain the desired cleaning effect should be replenished following the removal of soil from the bath. Overuse should be avoided.

The cleaning effect of the baths cannot be satisfactorily monitored by the methods in use at the present time. Conductivity and pH measurement or titration pick up only the inorganic components. Accordingly, these methods cannot be used for salt-containing cleaning preparations.

Another disadvantage of these methods is that they do not include the surfactant system.

Besides the surfactants, determination of the COD (chemical oxygen demand) or TOC (total oxidizable carbon) value also encompasses all other organic bath constituents, for example oil-containing soils, so that this process can only be used in selected cases.

Chemical analysis of the cleaning baths or even the determination of individual surfactants and classes of surfactants, for example hydrocarbon measurement, the BIAS or MBAS method, requires the presence of trained personnel. In addition, the analyses are time-consuming and therefore expensive.

The determination of residual grease on the surface to be cleaned or on test specimens by burning the carbon-containing material at elevated temperatures requires considerable outlay on equipment. In addition, the time required for one measurement is so considerable that on-line monitoring of the cleaning bath is hardly possible so that there is no opportunity for regulation of the cleaning process. In addition, it is only in a few cases that there is a clear correlation between residual soiling and the cleaning effect, so that the determination method cannot generally be applied.

Turbidity measurements also have disadvantages which prevent them from being universally applied. For example, they are seriously disrupted by emulsion formation and lose information value.

In view of the difficulties in monitoring cleaning baths by analysis, monitoring is often based on the quality of the subsequent treatment steps, for example on the quality of a metal layer applied to the metal surfaces by electrodeposition. The disadvantages of this approach are obvious, i.e. a large quantity of waste is produced in the event of failure.

For many subsequent treatment steps, for example electroplating, the metal surface has to be free from fats and oils. In many cases, the wettability of the surface with water is used as a measure of the quality of the cleaning step. However, the wettability test can not be universally applied because certain cleaners, more particularly neutral cleaners, produce water-repellent films on the surface to be cleaned in view of their special formulation. In addition, this test method can only be applied to parts of simple geometry, for example to flat plates. Moreover, the method does not allow differentiated evaluation of the condition of the cleaning bath.

The effect of the considerable difficulties involved in monitoring surfactant-containing cleaning baths is that replenishment is generally excessive and carried out too early and bath replacement is carried out too early. Apart from unnecessary costs, there are also considerable accumulations of waste water which efforts are being made to reduce for ecological and economic reasons.

DESCRIPTION OF THE INVENTION

Object of the Invention

Accordingly, the problem addressed by the present invention was to provide a process of the type mentioned at the beginning which would enable the degree of soiling of the bath and the cleaning reserve to be accurately measured both economically and quickly so that replenishment of the cleaning preparation could be measured more accurately and the amount of rinsing water required could be reduced. It would be possible in this way to reduce the number of bath changes and regeneration steps, the amount of cleaning preparation required and the quantity of waste water accumulating while, at the same time, retraining or improving the quality of cleaning. In addition the process according to the invention would be universally applicable. It could be operated on-line and continuously so that it would provide up-to-date results at short notice and would be suitable for automatic control, for example automatically controlled replenishment. A very important requirement is that the measurement should provide a result which correlates to a far greater extent than in known processes with the required value, namely the degree of soiling of the bath, the cleaning reserve and the quality of the subsequent treatment step, for example paintability and electroplatability. The cleaning reserve is essentially understood to be the ratio between the cleaning preparation and the various soils in the cleaning bath.

SUMMARY OF THE INVENTION

According to the invention, the solution to this problem is characterized in that, as a measure of the actual cleaning reserve of the cleaning liquid, a value correlated with the dynamic surface tension is measured with a bubble tensiometer which is operated with sufficiently constant gas streams, more particularly air streams, the results obtained are compared with a preset value obtained by calibration for the cleaning preparation used and servicing measures for the cleaning liquid, more particularly its regeneration and/or replenishment of the cleaning preparation, are carried out in dependence upon the outcome of this comparison. In the context of the present invention, standard bath-servicing facilities include inter alia skimmers, separators, oil separators, centrifuges, evaporators or membrane techniques. Servicing measures can be taken to mean an increase in the ratio of cleaning preparation to bath soil.

It has surprisingly been found that, in a variety of cleaning systems, the measurements obtained with a bubble tensiometer correlate very closely with the cleaning reserve, so that surfactant-containing cleaning baths can be monitored very much more accurately.

Methods for measuring the static surface tension, for example the ring method or the Wilhelmy method, cannot be applied here on account of the various soil types and the heterogeneity of the soiled cleaning bath. The results obtained by these methods cannot be used for determining the cleaning reserve and the level of soiling of the bath.

DESCRIPTION OF PREFERRED EMBODIMENTS

Particularly good resolution of the measuring signal is obtained by carrying out the measurement on a sample of the cleaning liquid cooled to a temperature of 20° to 60° C. and, more particularly, to a temperature of around 40° C. A further improvement in the resolving power is achieved if the measurement is carried out on a sample of the cleaning liquid diluted with water in a ratio of up to 1:10 and, more particularly, in a ratio of 1:0.5 to 1:2. In terms of process technology, these improvements in the resolving power can be achieved particularly favorably by carrying out the measurement in a sidestream to which water is added at such a temperature and in such a quantity that the degree of cooling and dilution required for the measurement is achieved.

In the regeneration of the cleaning bath, the oil present therein is often removed by membrane filtration and, more particularly, by ultrafiltration. This method of regeneration is particularly favorable because more than 95% of the oil present is normally removed. The oil-free permeate may be used for a new cleaning cycle. However, not only the oil components, but also part of the surfactants present in the cleaning bath are retained by the filtration membrane. The quantity of surfactants retained depends upon numerous parameters and hence varies. Accordingly, the cleaning preparation or individual components thereof have to be replenished. Since, hitherto, the surfactant content of the permeate could never be accurately determined, overdispensing was always the rule for safety reasons. In one embodiment of the present invention, therefore, the soiled cleaning liquid is regenerated by one of the usual methods, for example ultrafiltration, the dynamic surface tension of the treated solution, i.e. the permeate in the case of ultrafiltration, is measured, the surface-active cleaning components are introduced into the permeate in accordance with the result of the measurement, particularly in the course of a continuous measurement, and the regenerated cleaning liquid obtained is reused.

In another embodiment of the invention, a very much better criterion for the electroplatability of degreased metal surfaces is obtained if, during the degreasing/cleaning of metal surfaces to be electroplated in a following step, the dynamic surface tension of the cleaning liquid is continuously measured and servicing measures for the cleaning liquid, more particularly its replacement, are carried out whenever a particular set value is exceeded. According to the invention, electroplatability can be very accurately determined in contrast to known methods.

However, the process according to the invention can also be used for the preparation of fresh cleaning solutions. This is another reflection of the universal character of the process according to the invention. In this case, the cleaning preparation is dispensed in accordance with the actual value of the measured dynamic surface tension.

However, the process according to the invention may also be carried out to save time and rinsing water in a subsequent rinse cycle. In this case, the dynamic surface tension of the rinsing water is measured and the rinse cycle is terminated when the measured value exceeds a preset maximum value.

The surface tension may be determined in two different ways. Firstly, the maximum pressure difference between the bubbles produced with the bubble tensiometer can be measured. On the other hand, the flow rate of the bubbles issuing from the bubble tensiometer can be measured. The constant gas streams can be produced either by regulating variable gas streams or by using uniformly operating pumps.

The present invention also relates to an arrangement for carrying out the process described above. In this arrangement, the solution to the problem addressed by the invention is characterized by the provision of capillaries which are connected to constant gas stream sources and which dip to equal depths into the washing liquid, being connected to a unit for determining the pressure or the frequency of pressure changes which, via an evaluation unit, controls a display and/or a unit for carrying out, more particularly automatically, servicing measures for the cleaning liquid.

To reduce the quantity of rinsing water, the evaluation unit of the arrangement according to the invention is connected to a control element which actuates the rinse cycle.

BRIEF DESCRIPTION OF THE DRAWINGS

Results and embodiments of the invention are described in more detail in the following with reference to the accompanying drawings, wherein.

The bubble tensiometer used in accordance with the invention is known per se and is described, for example, by F. J. Schork and W. H. Rey in *Journal of Applied Polymer Science*, Vol. 28, 1983, pages 407 to 430, so that it will only be briefly explained at this juncture.

The bubble tensiometer is suitable for measuring dynamic surface tensions. Using this method, it is possible to detect differences in the output signal, even above the critical micelle concentration, in the event of a change in the concentration of surfactant. The bubble frequency and the maximum bubble pressure, for example, are suitable as output signals which can be directly linked to the dynamic surface tension and hence to the concentration of surfactant. If two capillaries with openings of different width are used instead of one capillary, the maximum difference in bubble pressure between the two capillaries may be used as a measuring signal, the pressure difference decreasing with decreasing dynamic surface tension.

Figure 1:
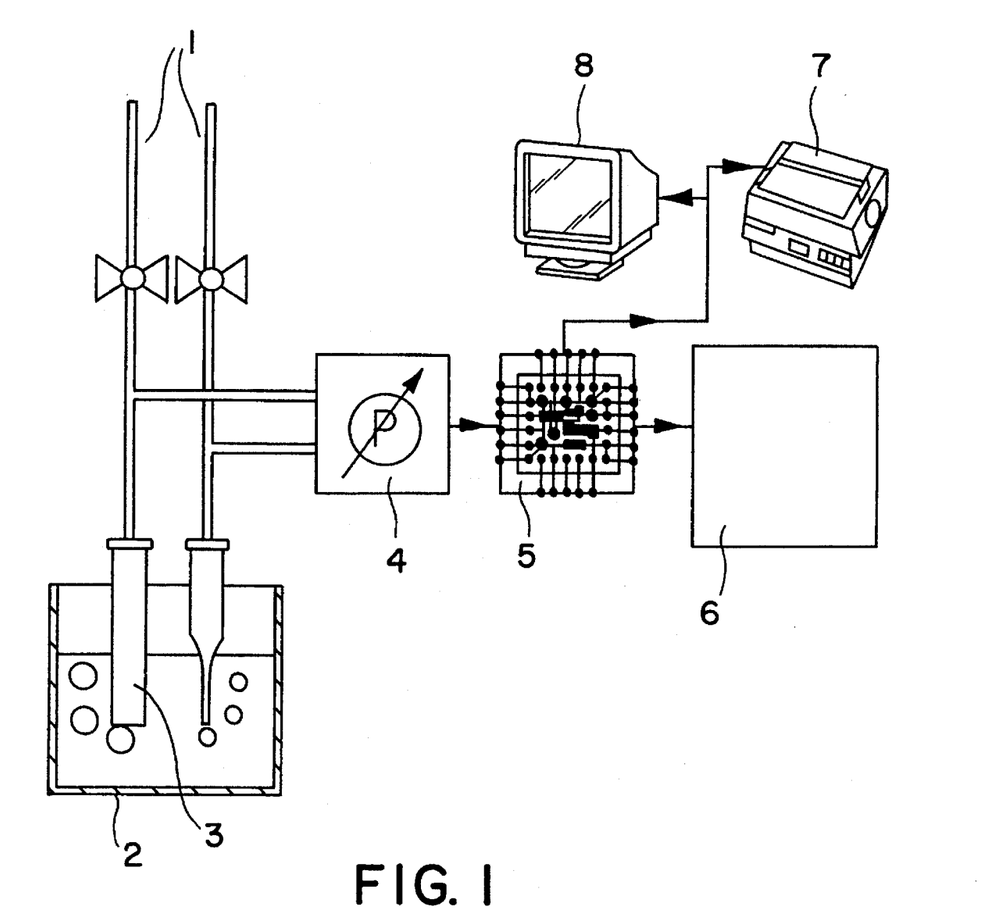
FIG. 1 diagrammatically illustrates a measuring arrangement.

The construction of a typical bubble tensiometer is shown in FIG. 1. Through the controlled air streams, air 1 is introduced into the solution 2 under defined pressure and volume conditions and escapes from the lower ends of the capillaries 3 in the form of bubbles. An electronic unit 4 for measuring pressure differences produces an electrically processable signal which is fed into a central computing unit 5, for example in the form of a personal computer or any other electronic unit suitable for process control. Depending on whether the processed signal exceeds or falls below preselected limits, a control unit 6 initiates control measures, such as replenishment, an indication of the exhaustion of the cleaning effect, regeneration, the end of replenishment and any other measures which are necessary for maintaining the cleaning properties of the metal cleaning bath. A printer 7 and a monitor 8 are also provided for data output.

Figure 2:
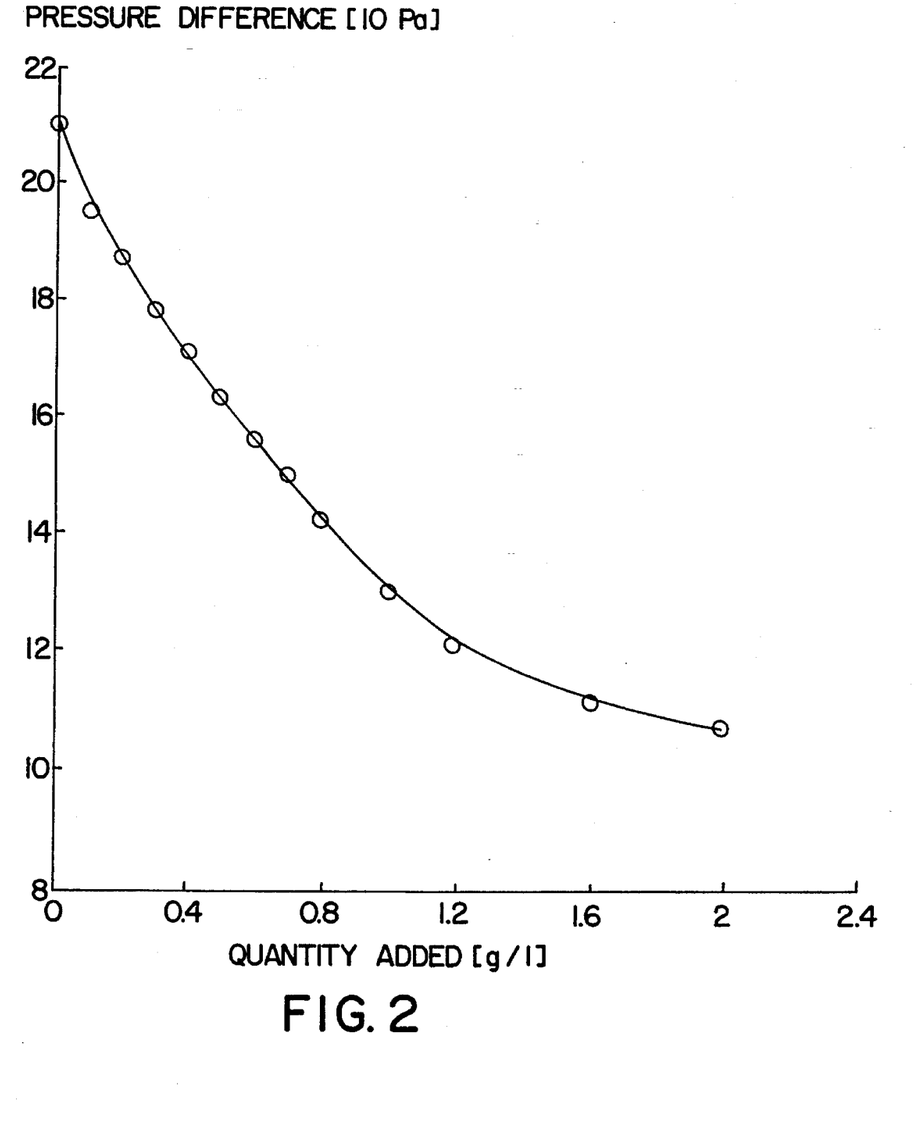
FIG. 2 shows results on the correlation between the measured values and the cleaning reserve.

FIG. 2 shows by way of example how the pressure difference measured by the bubble tensiometer decreases with increasing concentration of a preparation used for spray cleaning. The data were recorded from the permeate obtained after regeneration of a spent cleaning solution by ultrafiltration. The quantity of surfactant component additionally introduced, rather than the absolute quantity, is plotted on the abscissa. The good correlation and resolution are quite clear.

Figure 3:
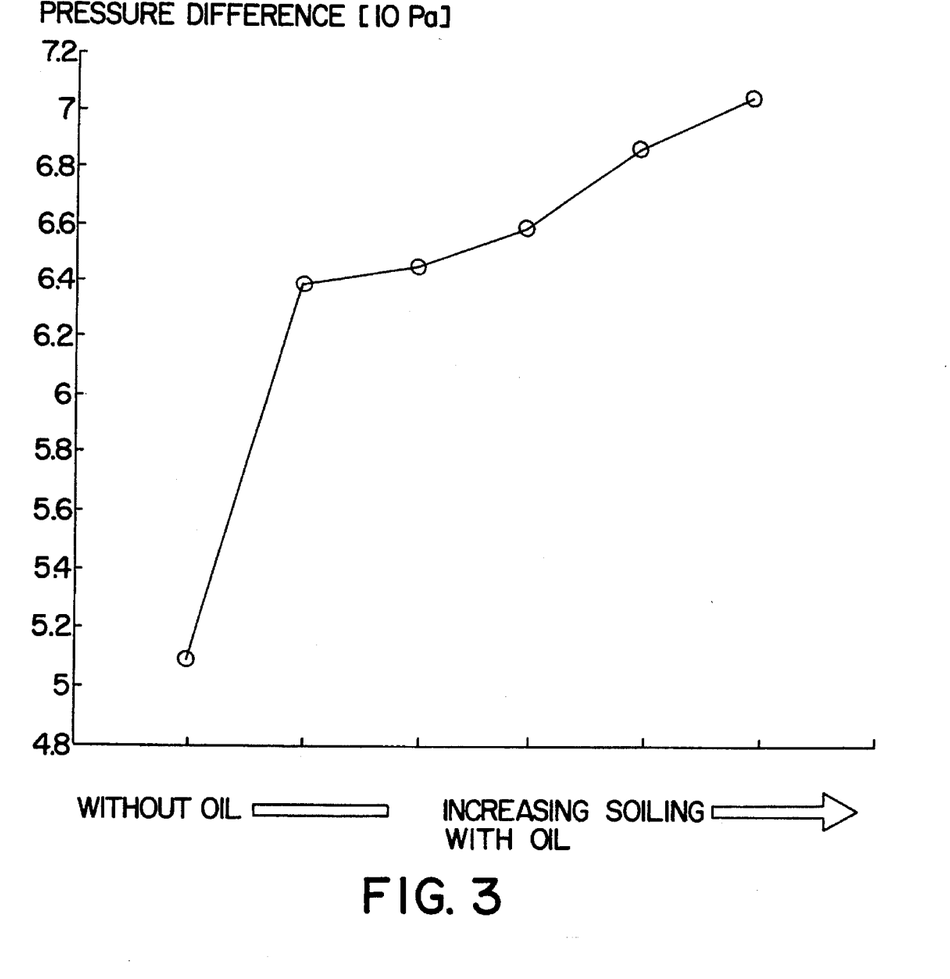
FIG. 3 shows results on the correlation between the measured values and the degree of soiling of the bath.

FIG. 3 shows how the pressure difference increases with increasing content of a bath-polluting treatment oil if, at the same time, the concentration of the alkaline immersion bath cleaner used is kept constant.

Figure 4:
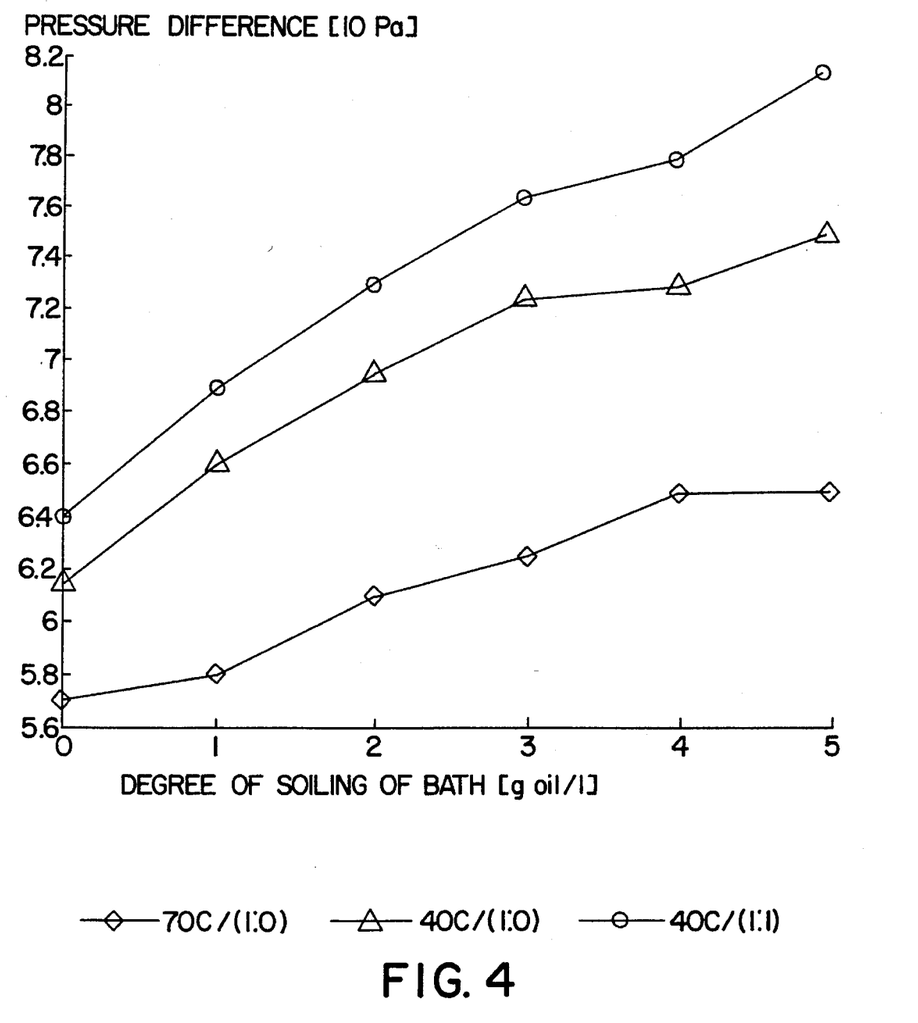
FIG. 4 shows the dependence of resolution on the temperature and dilution of the cleaning solution.

A basic process improvement which contributes towards distinctly better resolution of the signal differences has been found. This can be demonstrated with reference by way of example to a salt-free immersion bath cleaner. If the measurement is carried out under the temperature and concentration conditions of the cleaning bath, the analysis typically takes place at 70° to 80° C. in the concentrated solution. A signal recorded under these conditions for increasing levels of soil is shown in FIG. 4 (lower curve). If, however, the bath solution is analyzed at a lower temperature, for example at around 40° C., the dependence of the measuring signal on the degree of soiling of the bath is much clearer (FIG. 4, middle curve). A further improvement is obtained if, in addition, the solution is diluted.

Dilution in a ratio of approximately 1:1 has proved to be particularly favorable from the point of view of process and measurement technology. If it is carried out with cold tap water with a temperature of approximately 10° C., it also results in a reduction in temperature to 40° C. and, hence, leads to a particularly marked improvement in the resolution of the measured values in a single step which is easy to carry out by removal of a sidestream for substantially the same inflow of tap water (FIG. 4, upper curve).

Figure 5:
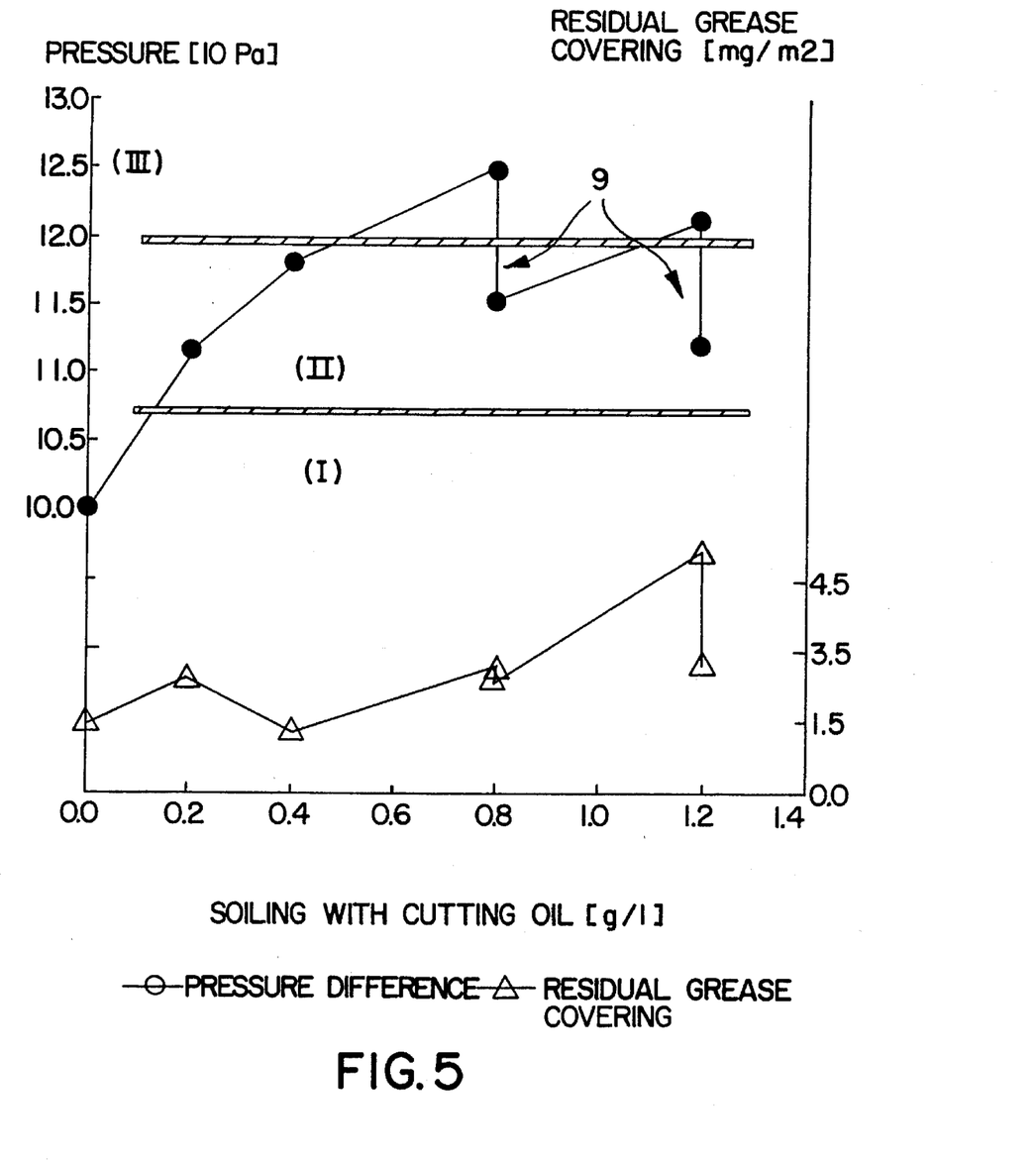
FIG. 5 shows the correlation of the measured values according to the invention and wettability with electroplatability.

FIG. 5, which relates by way of example to the treatment of brass plates with an alkaline dip cleaner to remove soil in the form of a commercial cutting oil prior to electroplating, shows that only the signal trend of the bubble tensiometer correlates clearly with subsequent nickel platability. Other parameters do not show any clear correlation with nickel platability, which is the objective of the cleaning process.

In this example (FIG. 5), the degree of soiling of the bath increases to 0.8 g/l of oil for an initially constant concentration of the cleaning preparation of 40 g/l. 10 g/l of cleaning preparation is then added. The level of soiling of the bath is then increased again to 1.2 g/l. Finally, another 10 g/l of cleaning preparation are added. The signal of the bubble tensiometer follows the increasing soiling of the bath exactly and shows a distinct and almost identical downward deflection for both replenishment steps 9. (Relatively high surfactant concentrations correspond to relatively low dynamic surface tensions and hence to smaller pressure differences.) The measurement was carried out at 40° C. and with a dilution ratio of 1:1 (solution:added water).

The parameter of practical relevance is the nickel platability of the cleaned brass plates. It exists in zones I and II of FIG. 5, but not in zone III. By nickel platability is meant the application of a firmly adhering nickel layer of satisfactory appearance by electrolytic deposition. Whereas there is a clear correlation between nickel platability and the level of the measuring signal for the measured values obtained with the bubble tensiometer, it is not possible with the other two parameters to make any predictions as to the possible nickel platability of the plates. The wettability of the plates is present only in zone I and not in zones II and III. Accordingly, it is no longer present even if the bath is only very slightly soiled although nickel plating is still possible.

The residual grease curve (lower curve in FIG. 5) also cannot be used to evaluate nickel platability, for example because replenishment does not always produce a change in the residual grease covering, but is still sufficient to restore the performance of the cleaning bath and to enable the plates to be subsequently nickel plated.

With the bubble tensiometer, however, the entire exemplary process of increasing bath soiling and replenishment can be clearly divided into three zones separated from one another by different pressure difference limits.

In zone I (FIG. 5), both wettability and nickel platability are present. In zone II below a pressure difference of around 120 Pa, wettability is no longer present in this example, although the crucial property of nickel platability has remained in place. Beyond the limit of 120 Pa (zone III), the performance of the cleaning bath is clearly no longer adequate; nickel plating is no longer possible. However, this property can be re-established by the two replenishment steps. At the same time, the bubble tensiometer records a fall in the measured value below the 120 Pa limit into zone II.

By virtue of the direct correlation, the excessive soiling of the bath can be detected and replenishment can be controlled by means of the bubble tensiometer without any need for other methods.

Figure 6:
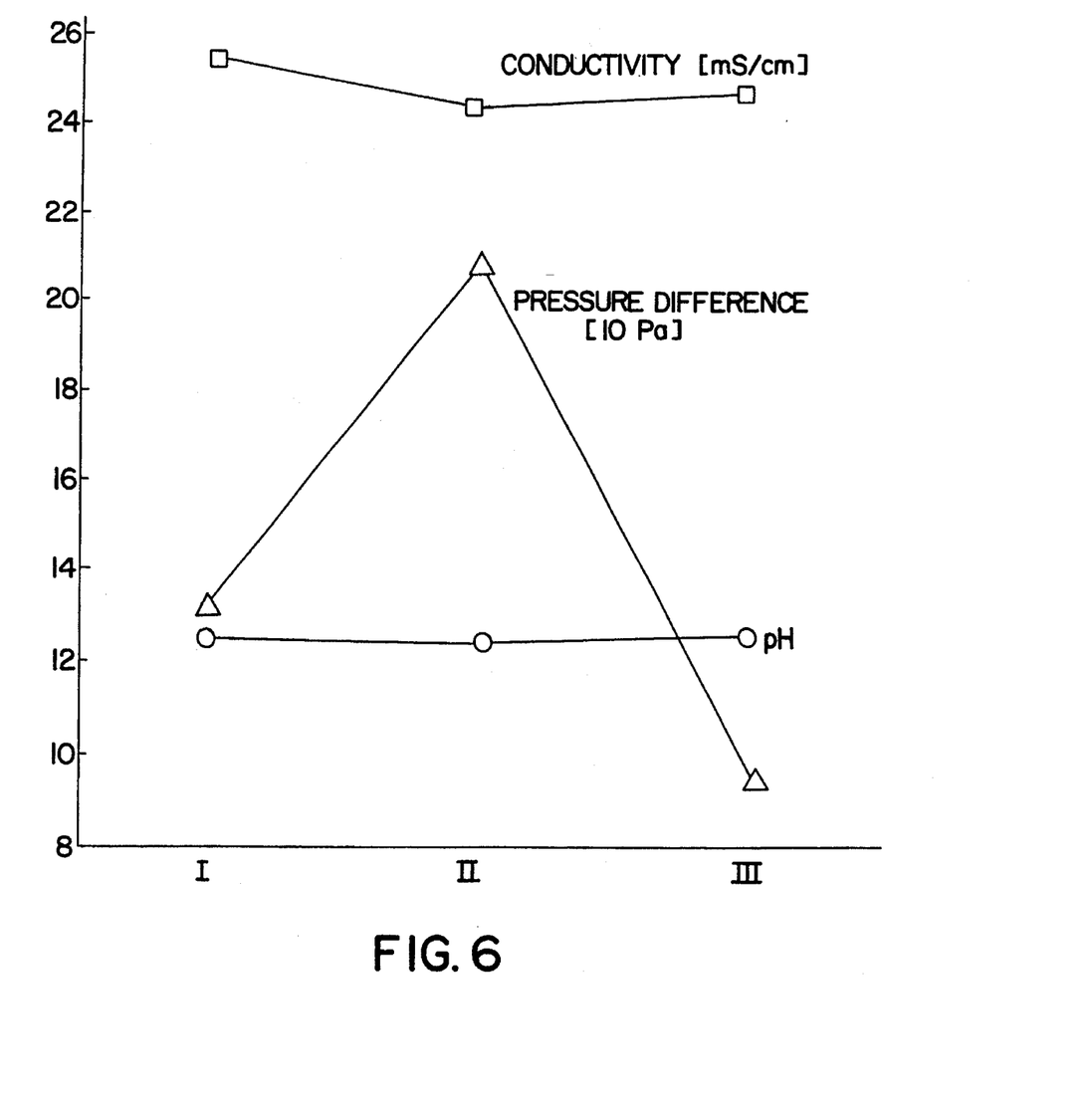
FIG. 6 shows the correlation of the measured values according to the invention, the pH value and conductivity with the cleaning reserve before and after bath regeneration.

Taking an alkaline spray cleaner as an example, FIG. 6 shows how the regeneration of a cleaning solution by an ultrafiltration step can be controlled by the use of the bubble tensiometer. In FIG. 6, the pressure differences measured with the bubble tensiometer are shown as bars for the unsoiled cleaning solution (zone I), the soiled solution after ultrafiltration (zone II) and after replenishment by sole addition of the surface-active cleaning component (zone III), in the present case 4 g of surfactant component/l. Both the original solution and the solution replenished with surfactant are suitable for cleaning whereas the ultrafiltered solution does not have adequate cleaning properties. Conductivity measurement (upper curve) and pH measurement (lower curve) produce substantially constant values for the three solutions and, accordingly, have no information value.

Accordingly, the present invention provides a suitable measuring process—above all in conjunction with the special diluting and cooling step—which can readily be carried out either in the cleaning bath itself or, better yet, in a sidestream with addition of cold water. The process according to the invention is suitable either on its own or in conjunction with other measures, for example conductivity measurement, pH measurement or titration, on the one hand for detecting soiling of the cleaning solution, primarily by oil, and on the other hand of guaranteeing—by measurement of the degree of soiling of the bath— control of the direct introduction of cleaning preparation into the solution or control of the beginning and end of necessary regeneration steps for the cleaning solution, including replenishment of the complete cleaner or its surface-active components. This is because the measuring signal of the bubble tensiometer provides a direct indication as to whether the required applicational properties, for example the nickel platability of cleaned plates, are in place.

The invention claimed is:

1. A process for degreasing and cleaning metal surfaces using a surfactant-containing water-based cleaning liquid in baths or by spray cleaning comprising the steps of:

(a) measuring the dynamic surface tension of a standardized cleaning liquid of known concentration using a bubble tensiometer operated with constant gas streams to establish a standard dynamic surface tension value;

(b) contacting said metal surfaces with a cleaning liquid;

(c) measuring the dynamic surface tension of said cleaning liquid using a bubble tensiometer operated with constant gas streams;

(d) comparing measurements obtained from steps (a) and (c) to determine both an amount of unused surfactant in said cleaning liquid as a measure of cleaning reserve of the cleaning liquid and a contaminant content in said cleaning liquid; and (e) regenerating said cleaning liquid based on results obtained from step (d).

2. The process of claim 1 wherein said step (c) is carried out on a sample of said cleaning liquid cooled to a temperature of from 20° to 60° C.

3. The process of claim 1 wherein said step (c) is carried out on a sample or said cleaning liquid diluted with water in a ratio of up to 1:10, respectively.

4. The process of claim 1 wherein step (c) is carried out on a sidestream of said cleaning liquid at a temperature of from 20° to 60° C., and wherein said cleaning liquid is diluted with water in a ratio of up to 1;10, respectively.

5. The process of claim 1 wherein said step (e) further includes removing an oil from said cleaning liquid by membrane filtration.

6. The process of claim 1 wherein said step (e) further includes introducing an amount of fresh suffactant into said cleaning liquid, said amount introduced being dependent upon said results obtained from said step (d).

7. The process of claim 1 further including rinsing said metal surfaces of said step (b) with water.

8. The process of claim 7 wherein said rinsing is controlled by measuring the dynamic surface tension of said water using said bubble tensiometer and terminating said rinsing when said dynamic surface tension of said water exceeds a standard value.

9. The process of claim 1 wherein said dynamic surface tension is measured by measuring the flow rate of bubbles exiting from said bubble tensiometer.

10. The process of claim 1 wherein said constant gas streams are controlled by regulating variable gas streams.

11. The process of claim 1 including controlling said constant gas streams with uniformly operating pumps.

* * * * *